US00PP16078P3

(12) United States Plant Patent
Hofmann

(10) Patent No.: US PP16,078 P3
(45) Date of Patent: Nov. 1, 2005

(54) **NEW GUINEA *IMPATIENS* PLANT NAMED 'FISNICS LIL'**

(50) Latin Name: *Impatiens hawkeri*
Varietal Denomination: Fisnics Lil

(75) Inventor: Birgit C. Hofmann, Bendorf (DE)

(73) Assignee: Florfis AG (CH)

( * ) Notice: Subject to any disclaimer, the term of this patent is extended or adjusted under 35 U.S.C. 154(b) by 85 days.

(21) Appl. No.: 10/829,353

(22) Filed: Apr. 22, 2004

(65) Prior Publication Data

US 2004/0237161 P1 Nov. 25, 2004

(30) Foreign Application Priority Data

Apr. 22, 2003 (CH) ..... 03-1990

(51) Int. Cl.[7] ..... A01H 5/00

(52) U.S. Cl. ..... Plt./318

(58) Field of Search ..... Plt./318

*Primary Examiner*—Kent Bell
(74) *Attorney, Agent, or Firm*—Foley & Lardner, LLP

(57) ABSTRACT

A new and distinct cultivar of New Guinea *Impatiens* plant named 'Fisnics Lil' particularly characterized by the combined features of uniform, brilliant purple flower color; large, round flowers on relatively long peduncles; intense medium green foliage, relatively large leaves; medium to tall, round and bushy plant habit; early to medium flowering response; and suitable both for sale as a flowering pot plant and as a relatively weather tolerant outdoor plant.

1 Drawing Sheet

Genus and species of the plant claimed: *Impatiens hawkeri.*

Variety denomination: 'Fisnics Lil'.

BACKGROUND OF THE INVENTION

The present invention comprises a new and distinct cultivar of New Guinea *Impatiens,* botanically known as *Impatiens hawkeri*, and hereinafter referred to by the cultivar name 'Fisnics Lil'.

'Fisnics Lil' is a product of a planned breeding program and originated from a hybridization made by the inventor, Birgit C. Hofmann, in a controlled breeding program in Hillscheid, Germany, in 2000.

The female parent was the commercial variety 'Logia' (U.S. Plant Pat. No. 11,935, under the variety denomination 'Kilogia'), characterized by red-purple flower color, medium green foliage, and roughly medium sized plant habit.

The male parent was the variety 'Celebration Lavender Glow' (U.S. Plant Pat. No. 11,652, under the denomination 'Balcelavgo'), having light purple flower color, medium green foliage, relatively small leaves, and medium sized plant habit.

'Fisnics Lil' was discovered and selected as one flowering plant within the progeny of the stated cross by the inventor in April 2001 in a greenhouse in Galdar, Gran Canaria, Spain.

The first act of vegetative or asexual reproduction of 'Fisnics Lil' was accomplished when cuttings were taken from the initial selection in July 2001 in a controlled environment in Galdar, Gran Canaria, Spain, by, or under the supervision of, Birgit Hofmann.

Horticultural examination of plants grown from these cuttings initiated in spring of 2002 in Hillscheid, Germany, and continuing thereafter, has demonstrated that the combination of characteristics as herein disclosed for 'Fisnics Lil' are firmly fixed and are retained through successive generations of asexual reproduction. The new cultivar reproduces true to type.

'Fisnics Lil' has not been observed under all possible environmental conditions. The phenotype may vary significantly with variations in environment such as temperature, light intensity and day length, without, however, any variation in genotype. The following observations, measurements, and comparisons describe plants grown in Hillscheid, Federal Republic of Germany, under greenhouse conditions which approximate those generally used in commercial practice.

BRIEF SUMMARY OF THE INVENTION

The following traits have been repeatedly observed and are determined to be basic characteristics of 'Fisnics Lil', which in combination distinguish this *Impatiens* as a new and distinct cultivar:

1. Uniform, brilliant purple flower color;
2. Large, round flowers on relatively long peduncles;
3. Intense medium green foliage, relatively large leaves;
4. Medium to tall, round and bushy plant habit;
5. Early to medium flowering response; and
6. Suitable both for sale as a flowering pot plant and as a relatively weather tolerant outdoor plant.

Of the many commercial cultivars known to the inventor, the most similar in comparison to 'Fisnics Lil' are the parental varieties 'Kilogia' and 'Balcelavgo', and the variety 'Papete' (U.S. Plant Pat. No. 8,457).

In comparison to 'Kilogia', 'Fisnics Lil' has a more bluish hue of flower color, larger flowers, larger leaves, and somewhat stronger stems, while the overall plant size is roughly similar.

In comparison to 'Balcelavgo', 'Fisnics Lil' has deeper purple colored and somewhat larger flowers, and larger leaves.

In comparison to 'Papete', 'Fisnics Lil' has distinctly larger and flatter, not cup-shaped, flowers, similar or somewhat taller plant habit, and leaves with a faintly rippled structure, while those of 'Kipete' are often rugose.

BRIEF DESCRIPTION OF THE DRAWING

The accompanying photographic drawing shows typical flower and foliage characteristics of 'Fisnics Lil' with colors being as true as possible with illustrations of this type.

The photograph drawing shows a side view of a typical 'Fisnics Lil' plant.

DETAILED BOTANICAL DESCRIPTION

In the following description color references are made to The Royal Horticultural Society Colour Chart (R.H.S.). The color values were determined indoors from plants grown in Hillscheid, Federal Republic of Germany, under greenhouse conditions which approximate those generally used in commercial practice.

The description is based on plants which were planted as rooted cuttings in 12 cm pots in late February 2003, and then grown in the greenhouse at a minimum temperature of 16° C. Most observations and measurements were made after the beginning of flowering in mid May, when the plants were about 12 weeks old.

PLANT

General appearance and form:

*Plant habit.*—Medium to tall, round, bushy, and well-branched; growth is indeterminate, though weak after flowering begins.

*Height.*—16.8 cm.

*Width.*—32.3 cm.

*Number of branches.*—10–12.

*Length of branches.*—13–14 cm.

*Internode length.*—4.5–5.5 cm.

*Diameter of branches.*—5–7 mm.

*Stem color.*—Dark red, R.H.S. 185 A.

*Propagation.*—Usually terminal tips for cuttings.

*Rooting.*—Roots initiate in about 18 days at 22° C., from sticking to transplanting.

*Cultivation time.*—It takes about 10 weeks of growing time to produce a marketable flowering plant in a 12 cm container.

Foliage:

*Leaf arrangement.*—Primarily in whorls.

*Shape of leaf.*—Elliptic, with acute base and slightly acuminate tip.

*Surface.*—Glossy and weakly rippled.

*Margin.*—Slightly serrated, ciliated.

*Leaf length.*—12.8 cm.

*Leaf width.*—4.8 cm.

*Upper surface main color.*—Medium green, uniform, no variegation mature leaves darker than R.H.S. 137 A, young leaves R.H.S. 137 D.

*Veins on upper surface.*—R.H.S. 185 D or lighter.

*Lower surface color.*—R.H.S. 138 B (both young and mature leaves).

*Veins on lower surface.*—Color. R.H.S. 185 A.

*Petiole size.*—2.5 cm in length, 3–4 mm in diameter.

*Petiole color.*—Upper side R.H.S. 180 A, lower side R.H.S. 185 A.

INFLORESCENCE

*Flowering response.*—About 9 weeks after planting of rooted cuttings.

*Flowering season.*—Generally indeterminate, mainly from March to October, depending on light intensity.

Flower:

*Number of flowers per node.*—7–9, in various stages of development.

*Form of corolla.*—Single-type, 5 petals.

*Shape of corolla.*—Nearly round, with the petals overlapping, almost flat to very slightly cupped.

*Corolla size.*—Average length: 75 mm Average width: 73 mm.

*Shape of petals.*—Cordate, slightly lobed at the apex, the top petal (banner petal) possibly slightly cupped. Top petal: 29 mm long, 54 mm wide. Lateral petals: 33 mm long, 43 mm wide. Lower petals: 33 mm long, 48 mm wide.

*Texture.*—Smooth, velvety.

*Aspect.*—Mostly flat, the banner petal possibly slightly cupped.

*Color (general tonality from a distance of three meters).*—Uniform, bright purple.

*Ground color of upper surface.*—N74 A, no markings.

*Color of eye zone.*—Red, R.H.S. 46 B, small.

*Color of lower surface.*—N74 A to N74 B.

*Spur color.*—Reddish-brown, R.H.S. 185 B.

*Spur shape and size.*—Downwardly curved, 45–50 mm long, 3 mm in diameter at the flower end.

*Peduncle size.*—6.0–6.5 cm in length, 2 mm in diameter.

*Peduncle color.*—Reddish-brown, R.H.S. 185 A.

*Flower bud.*—23 mm in length, 14 mm in diameter, color R.H.S. N74 B.

Reproductive organs:

*Stamens.*—5 in number, upper surface color is mainly R.H.S. 66 C.

*Anthers.*—Fused, hooded.

*Pollen.*—Whitish-yellow, about R.H.S. 8 D.

*Style and stigma.*—5 in number, pale yellow, about R.H.S. 150 D.

*Ovary.*—5-celled, 5 mm long, surface color green, R.H.S. 141 C.

Disease/pest resistance/susceptibility: No observations to date.

I claim:

1. A new and distinct New Guinea *Impatiens* plant named 'Fisnics Lil' as described and illustrated herein.

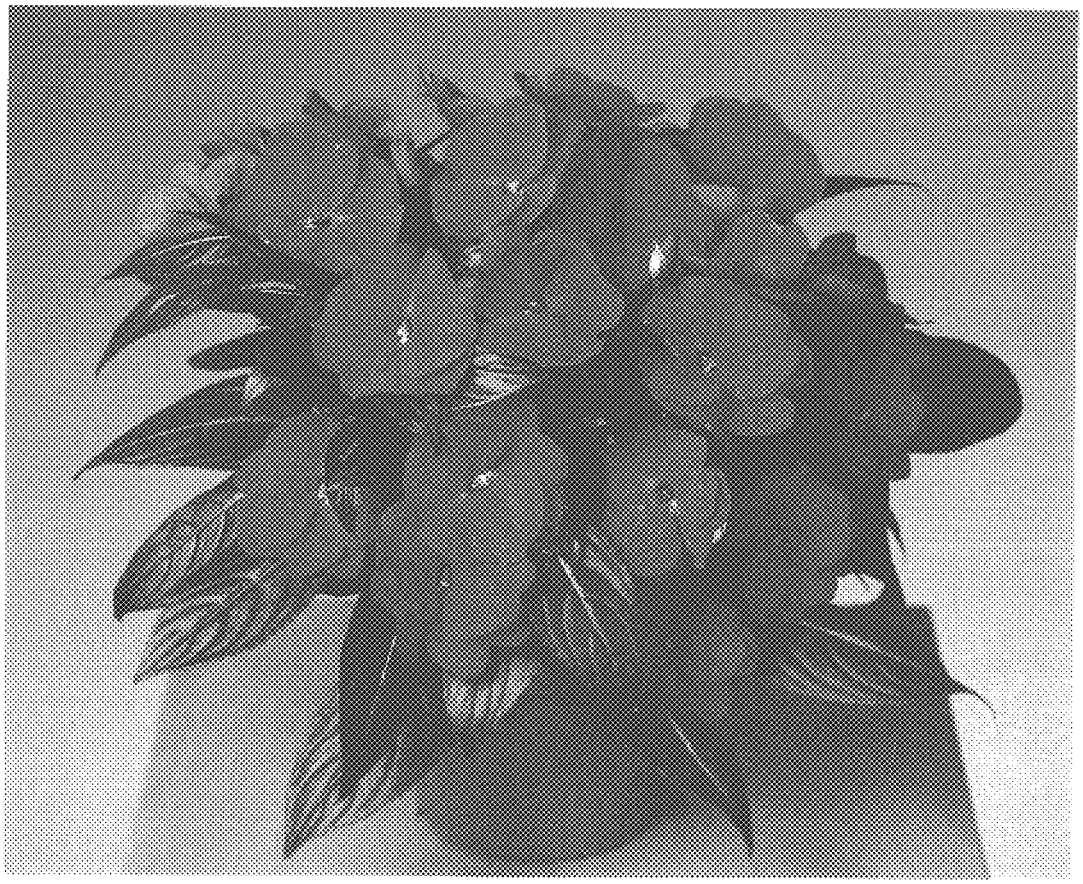

* * * * *